US006894191B1

(12) United States Patent
Kelkar et al.

(10) Patent No.: US 6,894,191 B1
(45) Date of Patent: May 17, 2005

(54) PROCESS FOR THE PREPARATION OF ARYLAMINES

(75) Inventors: Ashutosh Anant Kelkar, Maharashtra (IN); Nandkumar Manikrao Patil, Maharashtra (IN); Raghunath Vitthal Chaudhari, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/731,447

(22) Filed: Dec. 10, 2003

(51) Int. Cl.[7] ................. C07C 209/10; C07D 295/073; C07D 221/20; C07D 211/20
(52) U.S. Cl. ...................... 564/405; 544/174; 544/178; 546/16; 546/236; 546/240; 546/192
(58) Field of Search .................... 564/405; 544/174, 544/178; 546/16, 236, 240, 192

(56) References Cited

U.S. PATENT DOCUMENTS 5,831,128 A * 11/1998 Beller et al. ................ 564/405

6,235,938 B1 * 5/2001 Hartwig et al. ............. 564/407

OTHER PUBLICATIONS

Kelkar, et al., J. Org. Chem., vol. 32, No. 40, 2002, pp. 7143–7146, XP002279641.

E. Brenner et al., Tetrahedron Lett., vol. 41, 2000, pp. 2881–2884, XP004195693.

Goodbrand et al., J. Org. Chem., vol. 64, No. 2, 1999, pp. 670–674, XP002189995.

Quatch et al., Org. Lett., vol. 5, 2003, pp. 4397–4400, XO00227946.

* cited by examiner

*Primary Examiner*—Peter O'Sullivan
(74) *Attorney, Agent, or Firm*—Nixon & Vanderhye P.C.

(57) ABSTRACT

The present invention provides a process for the preparation of arylamines comprises reacting aryl halide and aryl amine/heterocyclic amine. The said process is carried out in the presence of a solvent, catalyst and a base.

29 Claims, No Drawings

PROCESS FOR THE PREPARATION OF ARYLAMINES

FIELD OF THE INVENTION

The present invention relates to a process for preparation of arylamines. More particularly the present invention relates to a process for preparing arylamines by contacting an aromatic halide and an aromatic primary amine in the presence of a catalyst and a base.

BACKGROUND OF THE INVENTION

Aryl amines are attractive targets for chemical synthesis because of their wide utility in fine chemicals, dyes and polymers. High purity triarylamines find application in xerographic photoreceptors where, as concentrated solid solutions in polymeric transport layers, they function as efficient hole conductors (U.S. Pat. Nos. 5,648,539 and 4,265,990). Triarylamines are also important to a number of emerging technologies like nonlinear optical chromophores useful in the design of integrated electrooptic switches and modulators (U.S. Pat. Nos. 5,654,482 & 5,723,671). Various methods have been described in the prior art for the preparation of arylamines. There are several reports in the prior art on the synthesis of aryl amines (U.S. Pat. Nos. 5,648,842 & 5,654,482). These and other prior art illustrate the Ullmann condensation reaction at high temperatures like 160° C. using non ligated cuprous oxide as catalyst. The drawback of these processes is that they are prone to produce troublesome impurities due to high operating temperatures, necessitating extensive purification. This becomes important for applications in charge transporting molecules in xerographic imaging and other electronic applications. European Patent Publication EP 0 617 005 A2 discloses the synthesis of certain aryl amines using copper catalyst in the form of metallic copper powder, copper sulfate, cuprous oxide, copper iodide or copper nitrate. However, the drawback of this process is also the use of very high temperatures such as 200° C. and very high reaction times such as 30 hours. Thus there is a need to develop improved catalyst system, which operates at lower reaction temperatures and preferably for shorter reaction times. There are several reports on the use of ligated copper catalyst, which operates at lower temperatures (~115° C.) (U.S. Pat. Nos. 5,705,697, 5,648,539, 5,723,671, 5,654,482 & 5,648,542). All these reports use only N-containing organic compounds and more specifically 1,10-phenanthroline as a ligand. There are few reports on the use of P-containing catalysts, which have good catalyst activity (Org. Lett. 3, 4315–4317, 2001), but no diphos ligands. However, in these cases use of preformed catalyst complex Cu (PPh$_3$)Br is necessary and no arylamine formation was observed when CuCl and free phosphine were used as catalyst system (Tet. Lett. 42, 4791–4793, 2001). However the drawback of this process is requirement of very high reaction time (24–32 h) using primary amines/ secondary amines as reactants.

Because of the commercial interest in arylamines, increasing academic as well as industrial attention has been paid towards research in developing new methods for their preparation. In view of the advantages and features of the present invention, the process of this invention would be a significant advancement in the current state of the art related to the synthesis of aryl amines.

OBJECTS OF THE INVENTION

The main object of the present invention is to provide an improved catalytic route for synthesis of arylamines with shorter reaction times using copper catalyst and bidentate phosphine ligands.

It is another object of the invention to provide a process for the preparation of a wide variety of arylamines with shorter reaction times, lower operating temperture and with high selectivity and rapid rate of formation.

SUMMARY OF THE INVENTION

Accordingly, the present invention provides a process for preparation of an arylamine comprising reacting a haloarene with an aromatic amine or a heterocyclic amine, the reaction being conducted in the presence of a catalyst comprising a copper compound, a ligand comprising a bidentate tertiary phosphorous compound, a base and a solvent.

In one embodiment of the invention, the haloarene has one halide radical and is represented by the formula Ar—X, wherein Ar represents an aromatic residue and X is selected from the group consisting of I, Br and Cl.

In another embodiment of the invention, the aromatic residue is selected from the group consisting of aromatic hydrocarbon aromatics such as benzene, biphenyl, naphthalene, and anthracene and nitrogen containing aromatics such as pyridine, bipyridine, and phenanthroline.

In another embodiment of the invention, the haloarene is of the formula

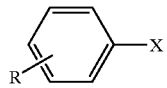

wherein R=H, alkyl, aryl, -OH, -OCH$_3$ and X=I, Br, Cl.

In another embodiment of the invention, the haloarene is of the formula

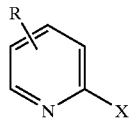

wherein X=I, Br, Cl; R=H, alkyl, aryl, -OH, -OCH$_3$

In another embodiment of the invention, the aryl amine is of the formula Ar—NH$_2$ wherein Ar represented an aromatic residue selected from the group consisting of benzene, biphenyl and naphthalene.

In yet another embodiment of the invention, the heterocyclic secondary amine is selected from the group consisting of pyridine, piperazine and morpholine.

In another embodiment of the invention, the amine compound is selected from the group consisting of compounds of the following formulae

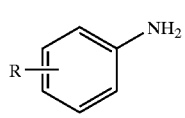

Formula 3

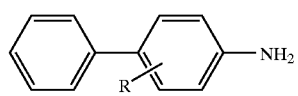

Formula 4 wherein R=H, alkyl, aryl, -OH.

Formula 5

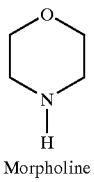

Morpholine

Formula 6

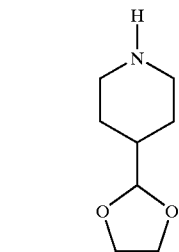

1, 4-dioxa-8-azasprio-[4.5] decane

Formula 7

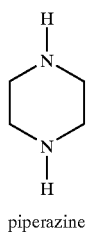

piperazine

Morpholine 1,4-dioxa-8-azasprio- [4,5]decane piperazine

In another embodiment of the invention, the solvent comprises a liquid that remains inert under the reaction conditions.

In a further embodiment of the invention, the solvent is selected from the group consisting of cyclohexane, toluene, benzene, 1,4-dioxane, t-butanol, N-methylpyrollidone, acetonitrile and Tetrahydrofuran.

In another embodiment of the invention, the copper compound is a copper complex with copper being in zero state or higher oxidation states.

In yet another embodiment of the invention, the copper compound is selected from the group consisting of copper salts of inorganic acids such as bromide, iodide, chloride, perchlorate.

In a further embodiment of the invention, the copper salt is selected from the group consisting of CuI, CuBr, CuCl, Cu(II)Br, CuOt-Bu, Cu(II)CO$_3$, and Cu(OAC)$_2$.

In another embodiment of the invention, the bidentate diphosphine ligand is selected from the group consisting of Ph$_2$P—CH$_2$—PPh$_2$[Bis(diphenylphosphino)methane (DPPM)], Ph$_2$P—CH=CH—PPh$_2$[Cis 1,2 Bis (diphenylphoshino)ethylene (DPPE)], Ph$_2$P—(CH2)$_3$—PPh$_2$[1,3-bis(diphenylphosphino)propane (DPPP)], Ph$_2$P—(CH2)$_4$—PPh$_2$[1,4-bis(diphenylphosphino)butane (DPPB)], Ph$_2$P—(CH2)$_5$—PPh$_2$[1,5-bis(diphenylphosphino)pantane (DPPT)] and Ph$_2$P—(CH2)$_6$—PPh$_2$[1,6-bis (diphenylphosphino)hexane (DPPH)].

In another embodiment, the ligand to metal mole ratio is in the range of 0.1 to 10, preferably 0.5–2.

In another embodiment, the amount of catalyst is in the range of 0.00001 to 1 molar equivalent with respect to the arylamine component added, the range of 0.001 to 1 mol being preferred.

In another embodiment, the base is selected from the group consisting of KOt-Bu, NaOt-Bu, KOH, NaOH, K$_2$CO$_3$, Cs$_2$CO$_3$, NaOMe, TEA, tri-t-butylamine, NaHCO$_3$, 1,8-Diazabicyclo[5.4.0]undec-7-ene (DBU); 1,5-Diazabicyclo[2.2.0]non-5-ene (DBN); 1,4-Diazabicyclo [2.2.2]octane (DABCO) 1,5-Diazabicyclo[4.3.0]none-5-ene and N,N-Dimethylbenzylamine.

In a further embodiment of the invention, the base is used in an amount sufficient to quench the halide from aryl halide or in excess.

In another embodiment, the temperature of the reaction in the range of 50–200° C., preferably in the range of 100 to 140° C.

In another embodiment, the reaction time is preferably in the range of 0.1 to 100 hours.

DETAILED DESCRIPTION OF THE INVENTION

The present invention provides a process for preparation of arylamines comprising reacting an aromatic halide with an aromatic amine or heterocyclic amine, the process being conducted in the presence of a catalyst, base and a solvent. The main advantage of the present invention is the shorter reaction time (~3 h) and lower operating temperature (~120° C.). This invention provides a catalytic process to obtain wide variety of arylamines with high selectivity and at rapid rates of formation.

Arylamines are obtained by reacting an aryl halide and aryl amine or heterocyclic amine. The aryl halide is an aromatic compound having one halide radical. Such compounds may be represented by formula Ar—X, where Ar represents an aromatic residue and X can be I or Br or Cl. The process is not limited to any particular aromatic system and any halide that can be represented by a Formula 1 and Formula 2 below and that can react under the conditions given in the present invention can be equally used. Suitable aromatics include aromatic hydrocarbon aromatics e.g. benzene, biphenyl, naphthalene, anthracene etc; nitrogen containing aromatics e.g. pyridine, bipyridine, phenanthroline etc. Suitable examples of such compounds are presented below.

Formula 1

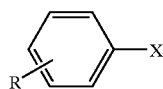

Where R=H, alkyl, aryl, -OH, -OCH$_3$, X=I, Br, Cl.

Formula 2

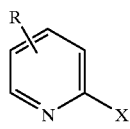

Where X=I, Br, Cl; R=H, alkyl, aryl, -OH, -OCH$_3$

The aryl amines are prepared by reacting an aryl halide and arylamine or heterocyclic amine. The arylamine compound is an aromatic compound having one NH$_2$ group. Such compounds can be represented by formula Ar—NH$_2$, where Ar represented an aromatic residue e.g. aromatic hydrocarbon such as benzene, biphenyl, naphthalene. Heterocyclic secondary amine is an organic compound containing at least one nitrogen atom, e.g. pyridine, piperazine, morpholine. The process is not limited to any particular aromatic system and any amine compound having the formula as stated above that can react under the conditions given in the present invention can be equally used. Suitable examples of such compounds are presented below.

Formula 3

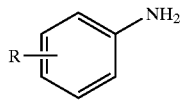

Formula 4

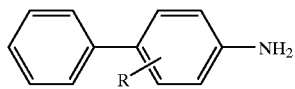

where R=H, alkyl, aryl, -OH.

Formula 5

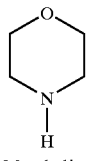

Morpholine

Formula 6

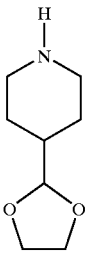

1, 4-dioxa-8-azasprio-[4.5] decane

Formula 7

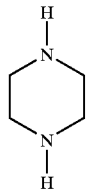

piperazine

The solvent is preferably a liquid that remain inert under the reaction conditions. Examples of preferred solvents include Cyclohexane, Toluene, Benzene, 1,4-Dioxane, t-Butanol, N-methylpyrollidone, Acetonitrile, and Tetrahydrofuran etc. There is no limit on the amount of solvent used and it can be selected based on process-related issue like stability, solubility of reactions, process economics.

The process of the invention is carried out in the presence of a catalyst containing a Copper complex. The metal can be present in the Zero state or in higher oxidation states. Variety of compounds can serve as source for the metal in the catalyst. Suitable examples include salts of inorganic acids e.g. bromide, iodide, chloride, perchlorate etc; The representative examples of such catalysts include CuI, CuBr, CuCl, Cu(II)Br, CuOt-Bu, Cu(II)CO$_3$, and Cu(OAC)$_2$.

The process of this invention is carried out in presence of a bidentate ligand containing at least two phosphorous atoms. Examples of diphosphine ligands include Ph$_2$P—CH$_2$—PPh$_2$[Bis(diphenylphosphino)methane (DPPM)], Ph$_2$P—CH=CH—PPh$_2$[Cis1,2Bis(diphenylphoshino)ethylene (DPPE)], Ph$_2$P—(CH2)$_3$—PPh$_2$[1,3-bis(diphenylphosphino)propane (DPPP)], Ph$_2$P—(CH2)$_4$—PPh$_2$[1,4-bis(diphenylphosphino)butane (DPPB)], Ph$_2$P—(CH2)$_5$—PPh$_2$[1,5-bis(diphenylphosphino)pantane (DPPT)], Ph$_2$P—(CH2)$_6$—PPh$_2$[1,6-bis(diphenylphosphino)hexane (DPPH)].

The ligand to metal mole ratio can be in the range of 0.1 to 10, 0.5–2 being preferred.

The amount of catalyst used in the process of this invention can vary within wide limits and there is no real upper level for it. Because of the very high activity of the catalytic system very low amounts of catalyst may be employed. Typically 0.00001 to 1 molar equivalent of copper catalyst can be employed with respect to the arylamine component added, the range of 0.001 to 1 mol being preferred.

The process according to the present invention is carried out in presence of base acting as a neutralizer for the hydrogen halide generated during the course of the reaction. Preferably the base used is a strong, inorganic, organic base such as KOt-Bu, NaOt-Bu, KOH, NaOH, K$_2$CO$_3$, Cs$_2$CO$_3$, NaOMe, TEA, tri-t-butylamine, NaHCO$_3$, 1,8-Diazabicyclo[5.4.0]undec-7-ene (DBU); 1,5-Diazabicyclo[2.2.0]non-5-ene (DBN); 1,4-Diazabicyclo[2.2.2]octane (DABCO) 1,5-Diazabicyclo[4.3.0]none-5-ene, N,N-Dimethylbenzylamine. The amount of base employed should be sufficiently enough to quench the halide from aryl halide. Alternatively an excess of base can be used if desired.

The temperature of the reaction is preferably in the range of 50–200° C., a temperature range of 100 to 140° C. being preferred.

The reaction time is not a true variable of and it depends on the nature and amounts of reactions, catalyst, solvent, pressure, temperature etc. Typically the reaction time of 0.1 to 100 hours can be used and may vary according to need.

It is obviously preferred that the compounds used, according to present invention, are stable and free from any other functionality which may react under the reaction condition or retard the formation of desired product.

The embodiments and examples described here to illustrate the catalyst activity and the process by no way limit the scope of the present invention and variety of similar type of substrates, that react in presence of said catalyst and condition, to give arylamine can be used.

The present invention is described herein below with reference to illustrative examples and should not be construed to limit the scope of the invention in any manner.

EXAMPLE 1

Amination reaction was carried out in a 50 ml capacity two neck round bottom flask. In a typical experiment, Toluene (23 ml) was charged to the round bottom flask followed by CuI (0.28 mmol), Bis(diphenylphosphino)methane (0.28 mmol), aniline (7.85 mmol), iodobenzene (16.48 mmols), and KOt-Bu (23.5 mmol). Reflux condenser was attached to the flask and the round bottom flask was flushed twice with nitrogen to ensure removal of air. Nitrogen balloon was attached to the condenser, to maintain nitrogen atmosphere during the reaction. The round bottom flask was then stirred by magnetic needle and heated to 115° C. in oil bath and the reaction was continued for 3.5 hours. After cooling to room temperature, the reaction solution was filtered to remove the precipitated base and washed with solvent. Initial and final samples were analyzed by GC and yield of triphenylamine was 62%.

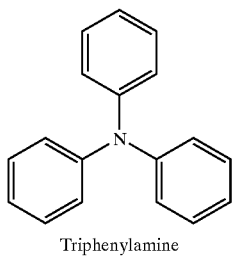

Triphenylamine

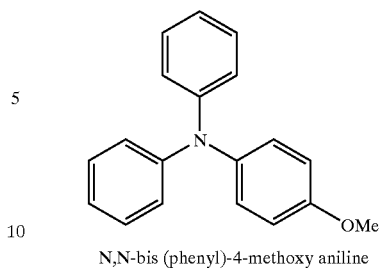

N,N-bis (phenyl)-4-methoxy aniline

EXAMPLE 2

Amination reaction was carried out in a 50 ml capacity two neck round bottom flask. In a typical experiment, Toluene (23 ml) was charged to the round bottom flask followed by CuI (0.28 mmol), Bis(diphenylphosphino)methane (0.28 mmol), aniline (7.85 mmol), p-methoxy iodobenzene (16.48 mmols), and KOt-Bu (23.5 mmol). Reflux condenser was attached to the flask and the round bottom flask was flushed twice with nitrogen to ensure removal of air. Nitrogen balloon was attached to the condenser, to maintain nitrogen atmosphere during the reaction. The round bottom flask was then stirred by magnetic needle and heated to 115° C. in oil bath and the reaction was continued for 3.5 hours. After cooling to room temperature, the reaction solution was filtered to remove the precipitated base and washed with solvent. The product was separated by column chromatography. The isolated yield of N,N-bis(4-methoxyphenyl)aniline was 74%.

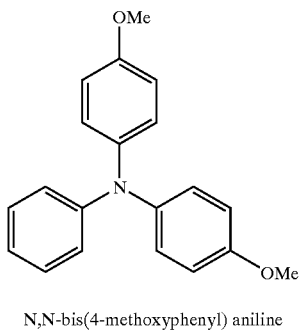

N,N-bis(4-methoxyphenyl) aniline

EXAMPLE 3

Amination reaction was carried out in a 50 ml capacity two neck round bottom flask. In a typical experiment, Toluene (23 ml) was charged to the round bottom flask followed by CuI (0.28 mmol), cis 1,2Bis(diphenylphosphino)ethylene (0.28 mmol), p-methoxyaniline (7.85 mmol), iodobenzene (16.48 mmols), and KOt-Bu (23.5 mmol). Reflux condenser was attached to the flask and the round bottom flask was flushed twice with nitrogen to ensure removal of air. Nitrogen balloon was attached to the condenser, to maintain nitrogen atmosphere during the reaction. The round bottom flask was then stirred by magnetic needle and heated to 115° C. in oil bath and the reaction was continued for 3.5 hours. After cooling to room temperature, the reaction solution was filtered to remove the precipitated base and washed with solvent. The product was separated by column chromatography. The isolated yield of N,N-bis(phenyl)-4-methoxy aniline was 78%.

EXAMPLE 4

Amination reaction was carried out in a 50 ml capacity two neck round bottom flask. In a typical experiment, Toluene (23 ml) was charged to the round bottom flask followed by CuI (0.28 mmol), 1,3-bis(diphenylphosphino)propane (DPPP) (0.28 mmol), aniline (7.85 mmol), iodobenzene (16.48 mmols), and KOt-Bu (23.5 mmol). Reflux condenser was attached to the flask and the round bottom flask was flushed twice with nitrogen to ensure removal of air. Nitrogen balloon was attached to the condenser, to maintain nitrogen atmosphere during the reaction. The round bottom flask was then stirred by magnetic needle and heated to 115° C. in oil bath and the reaction was continued for 3.5 hours. After cooling to room temperature, the reaction solution was filtered to remove the precipitated base and washed with solvent. Initial and final samples were analyzed by GC and yield of triphenylamine was 92%.

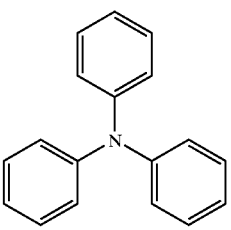

Triphenylamine

EXAMPLE 5

Amination reaction was carried out in a 50 ml capacity two neck round bottom flask. In a typical experiment, Toluene (23 ml) was charged to the round bottom flask followed by CuI (0.28 mmol), 1,6-bis(diphenylphosphino)hexane (0.28 mmol), aniline (7.85 mmol), p-methoxy iodobenzene (16.48 mmols), and KOt-Bu (23.5 mmol). Reflux condenser was attached to the flask and the round bottom flask was flushed twice with nitrogen to ensure removal of air. Nitrogen balloon was attached to the condenser, to maintain nitrogen atmosphere during the reaction. The round bottom flask was then stirred by magnetic needle and heated to 115° C. in oil bath and the reaction was continued for 3.5 hours. After cooling to room temperature, the reaction solution was filtered to remove the precipitated base and washed with solvent. The product was separated by column chromatography. The isolated yield of N,N-bis(4-methoxyphenyl)aniline was 87%.

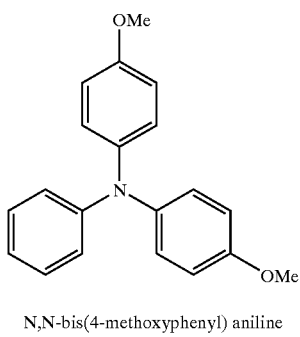

N,N-bis(4-methoxyphenyl) aniline

EXAMPLE 6

Amination reaction was carried out in a 50 ml capacity two neck round bottom flask. In a typical experiment, Toluene (23 ml) was charged to the round bottom flask followed by CuI (0.28 mmol), 1,3-bis(diphenylphosphino)propane (0.28 mmol), Morpholine (7.85 mmol), iodobenzene (16.48 mmols), and KOt-Bu (23.5 mmol). The Round bottom flask was flushed twice with nitrogen to ensure removal of air. The round bottom flask was then stirred by magnetic needle and heated to 115° C. in oil bath and the reaction was continued for 3.5 hours. After cooling to room temperature, the reaction solution was filtered to remove the precipitated base and washed with solvent. Product was separated by column chromatography and analyzed by NMR, IR and GC. The isolated yield of N-phenyl morpholine was 82%.

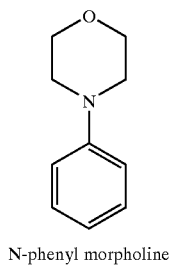

N-phenyl morpholine

EXAMPLE 7

Amination reaction was carried out in a 50 ml capacity two neck round bottom flask. In a typical experiment, Toluene (23 ml) was charged to the round bottom flask followed by CuI (0.28 mmol), 1,3-bis(diphenylphosphino)propane (0.28 mmol), piperazine (7.85 mmol), iodobenzene (16.48 mmols), and KOt-Bu (23.5 mmol). The Round bottom flask was flushed twice with nitrogen to ensure removal of air. The round bottom flask was then stirred by magnetic needle and heated to 115° C. in oil bath and the reaction was continued for 3.5 hours. After cooling to room temperature, the reaction solution was filtered to remove the precipitated base and washed with solvent. Product was separated by column chromatography and analyzed by NMR, IR and GC. The isolated yield of N,N'-diphenylpiperazine was 79%.

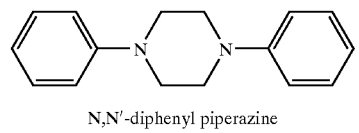

N,N'-diphenyl piperazine

EXAMPLE 8

Amination reaction was carried out in a 50 ml capacity two neck round bottom flask. In a typical experiment, Toluene (23 ml) was charged to the round bottom flask followed by CuI (0.28 mmol), Cis1,2-bis (diphenylphosphino)ethylene (0.28 mmol), Morpholine (7.85 mmol), iodobenzene (16.48 mmols), and KOt-Bu (23.5 mmol). The Round bottom flask was flushed twice with nitrogen to ensure removal of air. The round bottom flask was then stirred by magnetic needle and heated to 115° C. in oil bath and the reaction was continued for 3.5 hours. After cooling to room temperature, the reaction solution was filtered to remove the precipitated base and washed with solvent. Product was separated by column chromatography and analyzed by NMR, IR and GC. The isolated yield of N-phenyl morpholine was 75%.

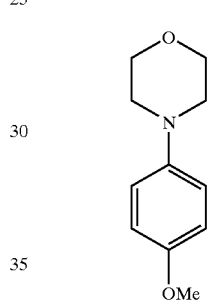

4-morpholinoanisole

We claim:

1. A process for preparation of an arylamine comprising reacting a haloarene with an aromatic amine or a heterocyclic amine, the reaction being conducted in the presence of a catalyst comprising a copper compound, a ligand comprising a bidentate tertiary phosphorous compound, a base and a solvent.

2. A process as claimed in claim 1 wherein the haloarene has one halide radical and is represented by the formula Ar—X, wherein Ar represents an aromatic residue and X is selected from the group consisting of I, Br and Cl.

3. A process as claimed in claim 2 wherein the aromatic residue comprises a aromatic hydrocarbon aromatic selected from the group consisting of benzene, biphenyl, naphthalene and anthracene.

4. A process as claimed in claim 2 wherein the aromatic residue comprises a nitrogen containing aromatic selected from the group consisting of pyridine, bipyridine, and phenanthroline.

5. A process as claimed in claim 1 wherein the haloarene is of the formula

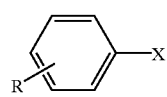

wherein R=H, alkyl, aryl, —OH, —OCH$_3$ and X=I, Br, Cl.

6. A process as claimed in claim 1 wherein the haloarene is of the formula

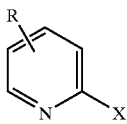

wherein X=I, Br, Cl; R=H, alkyl, aryl, —OH, —OCH$_3$.

7. A process as claimed in claim 1 wherein the aryl amine is of the formula Ar—NH$_2$ wherein Ar represented an aromatic residue selected from the group consisting of benzene, biphenyl and naphthalene.

8. A process as claimed in claim 1 wherein the heterocyclic amine is selected from the group consisting of pyridine, piperazine and morpholine.

9. A process as claimed in claim 1 wherein the amine compound is selected from the group consisting of compounds of the following formulae Formula 3

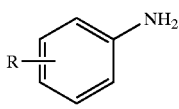

Formula 4

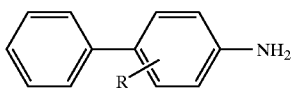

wherein R=H, alkyl, aryl, —OH

Formula 5

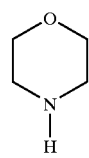

Morpholine

Formula 6

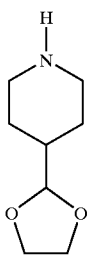

1, 4-dioxa-8-azasprio-[4.5] decane

Formula 7

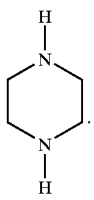

piperazine

10. A process as claimed in claim 1 wherein the solvent comprises a liquid that remains inert under the reaction conditions.

11. A process as claimed in claim 10 wherein the solvent is selected from the group consisting of cyclohexane, toluene, benzene, 1,4-dioxane, t-butanol, N-methylpyrollidone, acetonitrile and Tetrahydrofuran.

12. A process as claimed in claim 1 wherein the copper compound is a copper complex with copper being in zero state or higher oxidation states.

13. A process as claimed in claim 1 wherein the copper compound comprises a copper salt of an inorganic acid is selected from the group consisting of bromide, iodide, chloride, perchlorate.

14. A process as claimed in claim 1 wherein the copper salt is selected from the group consisting of CuI, CuBr, CuCl, Cu(II)Br, CuOt-Bu, Cu(II)CO$_3$, and Cu(OAC)$_2$.

15. A process as claimed in claim 1 wherein the bidentate diphosphine ligand is selected from the group consisting of Ph$_2$P—CH$_2$—PPh$_2$[Bis(diphenylphosphino)methane (DPPM)], Ph$_2$P—CH=CH—PPh$_2$[Cis1,2Bis(diphenylphoshino)ethylene (DPPE)], Ph$_2$P—(CH2)$_3$—PPh$_2$[1,3-bis(diphenylphosphino)propane (DPPP)], Ph$_2$P—(CH2)$_4$—PPh$_2$[1,4-bis(diphenylphosphino)butane (DPPB)], Ph$_2$P—(CH2)$_5$—PPh*$_2$[1,5-bis(diphenylphosphino)pantane (DPPT)] and Ph$_2$P—(CH2)$_6$—PPh$_2$[1,6-bis(diphenylphosphino)hexane (DPPH)].

16. A process as claimed in claim 1 wherein the ligand to metal mole ratio is in the range of 0.1 to 10.

17. A process as claimed in claim 16 wherein the ligand to metal mole ratio is in the range of 0.5–2.

18. A process as claimed in claim 1 wherein the amount of catalyst is in the range of 0.00001 to 1 molar equivalent with respect to the arylamine component added.

19. A process as claimed in claim 18 wherein the amount of catalyst is in the range of 0.001 to 1 mol with respect to the arylamine component added.

20. A process as claimed in claim 1 wherein the base is selected from the group consisting of KOt-Bu, NaOt-Bu, KOH, NaOH, K$_2$CO$_3$, Cs$_2$CO$_3$, NaOMe, TEA, tri-t-butylamine, NaHCO$_3$, 1,8-Diazabicyclo[5.4.0]undec-7-ene (DBU); 1,5-Diazabicyclo[2.2.0]non-5-ene (DBN); 1,4-Diazabicyclo[2.2.2]octane (DABCO) 1,5-Diazabicyclo[4.3.0]none-5-ene and N,N-Dimethylbenzylamine.

21. A process as claimed in claim 1 wherein the base is used in an amount sufficient to quench the halide from aryl halide or in excess.

22. A process as claimed in claim 1 wherein the temperature of the reaction in the range of 50–200° C.

23. A process as claimed in claim 1 wherein the temperature of the reaction in the range of 100 to 140° C.

24. A process as claimed in claim 1 wherein the temperature of the reaction in the range of 0.1 to 100 hours.

25. A process as claimed in claim 1 wherein the haloarene is iodobenzene.

26. A process as claimed in claim 1 wherein the base is selected from KOt-Bu and NaOt-Bu.

27. A process as claimed in claim 1 wherein the catalyst comprises a Cu(I) or Cu(II) salt or a copper complex with bidentate phosphorous ligand.

28. A process as claimed in claim 1 wherein the bidentate phosphine compound used is selected from the group consisting of 1,1-Bis(diphenylphosphino)methane, Cis1,2Bis(diphenylphoshino)ethylene, 1,2-bis(diphenylphosphino)ethane, 1,3-bis(diphenylphosphino)propane, 1,4-bis(diphenylphosphino)butane, 1,5-bis(diphenylphosphino)pentane and 1,6-bis(diphenylphosphino)hexane (DPPH).

29. A process as claimed in claim 1 wherein the solvent is selected from toluene and xylene.

* * * * *